United States Patent [19]

Rhodes et al.

[11] Patent Number: 5,369,977
[45] Date of Patent: Dec. 6, 1994

[54] GASEOUS DETECTION SYSTEM

[75] Inventors: Kevin Rhodes, Newton; Ernie Vandenwijngaert, Logan, both of Utah

[73] Assignee: Lundahl Instruments, Inc., Logan, Utah

[21] Appl. No.: 187,779

[22] Filed: Jan. 24, 1994

Related U.S. Application Data

[63] Continuation of Ser. No. 932,604, Sep. 30, 1992, abandoned.

[51] Int. Cl.⁵ ............................................. G01N 31/08
[52] U.S. Cl. ................................. 73/23.3; 73/23.36; 73/23.41; 422/83; 422/84
[58] Field of Search ........................... 422/83–84, 422/89; 73/23.21, 23.31, 23.35–23.36, 23.41, 1 G, 23.3

[56] References Cited

U.S. PATENT DOCUMENTS

| | | | |
|---|---|---|---|
| 3,618,363 | 11/1971 | Kraus | 73/19.01 |
| 3,622,278 | 11/1971 | Elzinga | 422/84 |
| 3,785,774 | 1/1974 | Murphy | 422/84 |
| 3,951,855 | 4/1976 | Principe et al. | 73/23.3 |
| 4,090,078 | 5/1978 | Heim | 422/84 |
| 4,163,383 | 8/1979 | Vandersyde et al. | 422/84 |
| 4,177,668 | 12/1979 | Holmberg | 73/23.3 |
| 4,278,636 | 7/1981 | Voigt et al. | 422/84 |
| 4,391,777 | 7/1983 | Hutson | 422/84 |
| 4,809,810 | 3/1989 | Elfman et al. | 422/84 |
| 4,905,498 | 3/1990 | O'Donnell et al. | 73/23.35 |

*Primary Examiner*—Robert J. Warden
*Assistant Examiner*—Hien Tran
*Attorney, Agent, or Firm*—Rockey, Rifkin & Ryther

[57] ABSTRACT

A gaseous detection system for detecting the existence of a certain gas and further detecting a certain level or percentage of that certain gas within a prescribed environment. An example is the use of the gas detection system in a motor vehicle or elsewhere to determine when the driver of the motor vehicle may be driving under the influence of alcohol, and alternatively, for providing signals that may be used for evidentiary purposes of the alcohol content in the breath of the driver. The system includes a sensor unit for sensing ethanol in the atmospheric contents of the test person's breath and utilizing fresh air and a reference gas to determine the amount, if any, of blood-alcohol content of a person for evidentiary or other purposes.

8 Claims, 6 Drawing Sheets

GASEOUS DETECTION SYSTEM

This is a continuation of copending application Ser. No. 07/932,604 filed on Sep. 30, 1992, now abandoned.

BACKGROUND OF THE INVENTION

This invention relates generally to a gaseous detection system for detecting the presence and determining the level of a pre-selected gas. One particular application of this system relates to alcohol detection and, more particulary, to the detection of the alcohol or ethanol content of the breath of a person. The blood-alcohol content, as determined by this invention, may be used for evidentiary purposes. The blood-alcohol content may be displayed on a digital read-out system or other methods of display as desired.

It has long been recognized that detection of certain gases is necessary for the safety or well-being of human life. Coal miners used canaries to warn them of the presence of life-endangering gases. The art of gas detection has progressed until today, there are many systems of gas detection (i.e. infrared, gas chromatography, etc.). These systems to date have required costly and elaborate equipment and reference materials to be both accurate and reliable. One primary use for such detection systems has been to detect the presence of breath-alcohol (i.e. ethanol) in the exhalation of a person.

As previously noted in U.S. Pat. No. 4,905,498, issued to Jack O'Donnell, et al., a novel system was developed to use ambient air as the carrier of the gas to be detected. A number of valves and pneumatic pathways were used to control the function of the detection or isolation unit and the functioning of a sensor unit with respect thereto. The comparison operation, carried out in U.S. Pat. No. 4,905,498, made use of a dynamically established reference value that was renewed with each cycle and was referenced to the sensor's operation. This system changed the accuracy of gas sensors using chromatograph tubes to enable accurate readings without the requirement of pure reference gases for carrying the gas to be detected.

The gas detection system of this invention provides an improved, stable analysis of the discernable blood-alcohol content of a person's breath sample displayed on a digital read-out device or ether display mode. The analysis is accurate enough to be used for evidentiary or like purposes.

Although the following description of the best mode relates to the use of the invention in connection with the presence of ethanol in a person's breath, the system, with minor modifications, can also be utilized as a gas detection system for detecting the presence of other selected gases in most environments where such testing is done today.

BRIEF DESCRIPTION OF THE DRAWINGS

These and other attributes of the invention will become more clear upon a thorough review and study of the following description of the best mode for carrying out the invention, wherein.

BEST MODE FOR CARRYING OUT THE INVENTION

The invention will now be described as a system designed to detect breath alcohol (i.e. ethanol) in the breath of a person. The claims are not to be so limited. The embodiment hereof includes pneumatic and electronic elements and components. The unit also contains mathematical processing circuitry. Chips will normally comprise the greater part of the control and processing circuitry. A detailed description of the processing circuits will not be provided because the circuits shown in FIGS. 3a–e are well known to those persons skilled in the art, and various electronic means and systems may be used to control the functions, including integration of signals, etc. needed in this invention.

Upon being activated by an on/off switch not shown, the unit will apply heat to the sensor and the chromatograph tube and other units within the framework of the device to enable them to reach operating temperatures; which temperatures may vary, depending upon the requirements of the components being used.

A sub block control in the processor (34) in FIGS. 3a–e, is energized and will include a self-test system for testing the temperature input voltage, pressure values, sensor operation and any other values requiring testing before operation.

Figure 1:
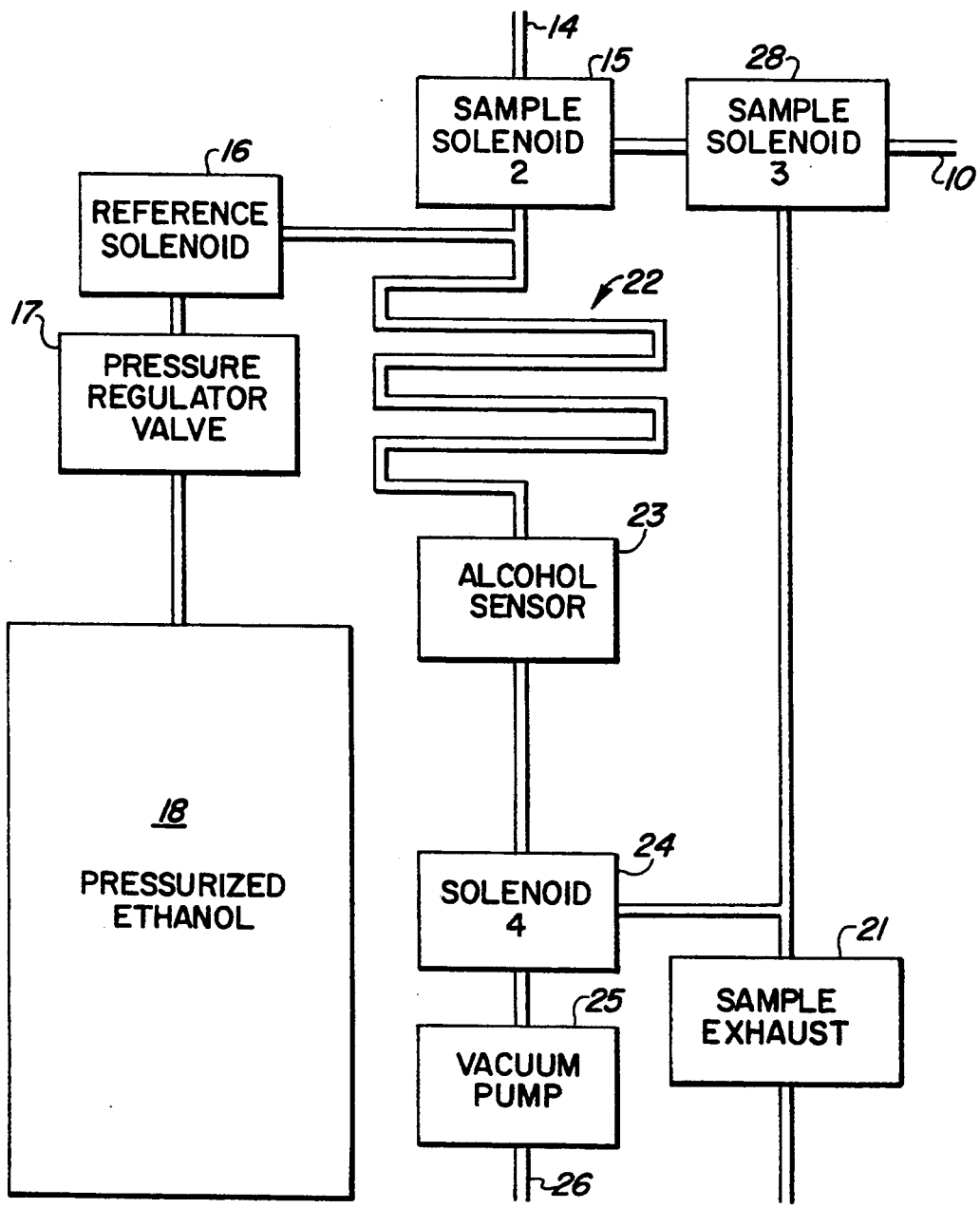
FIG. 1 comprises a schematic diagram of the flow system and the pneumatic and controls therefore.
Figure 2:
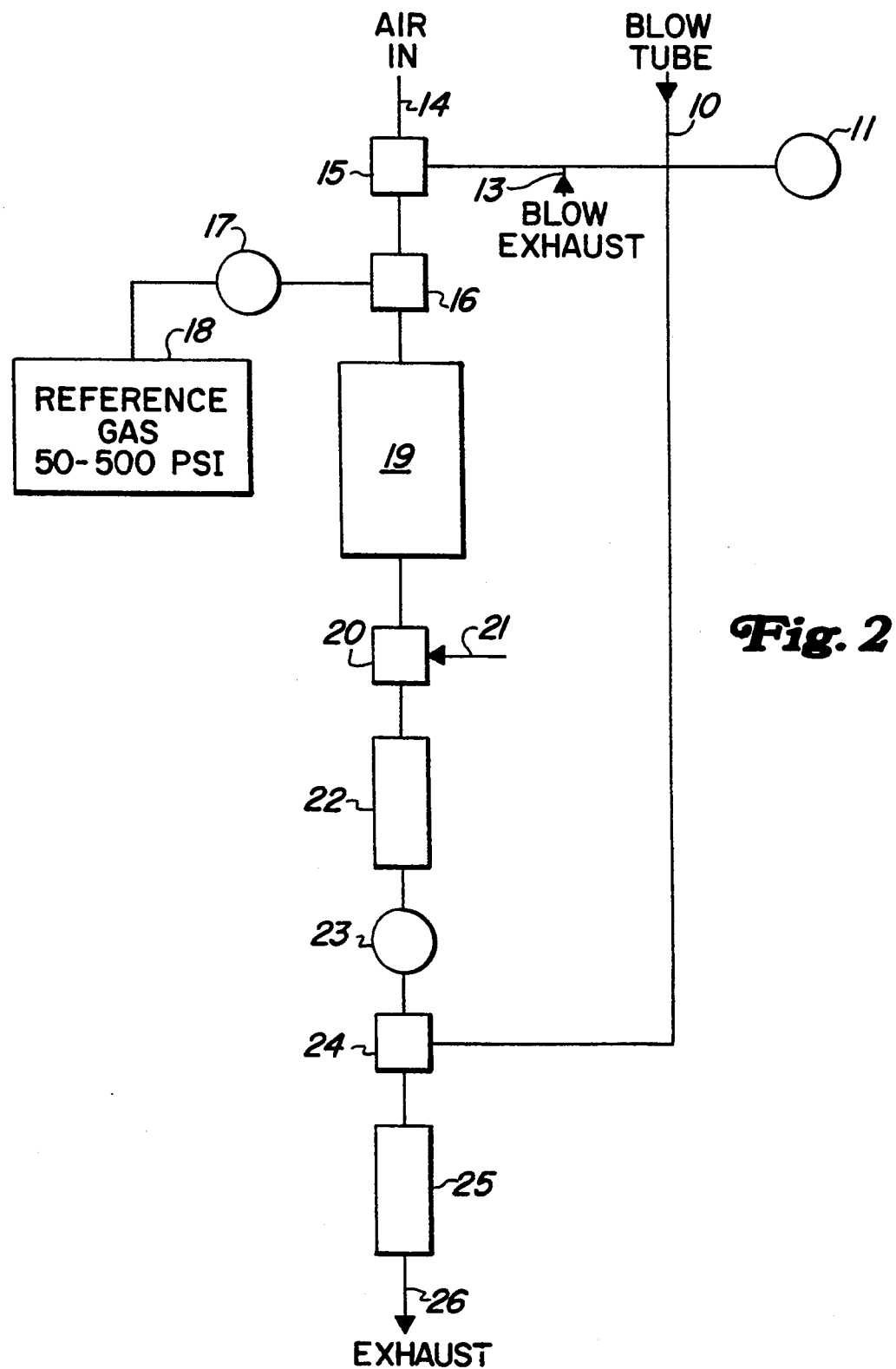
FIG. 2 comprises a block diagram of the flow of the gases in the system.
Figure 3A:
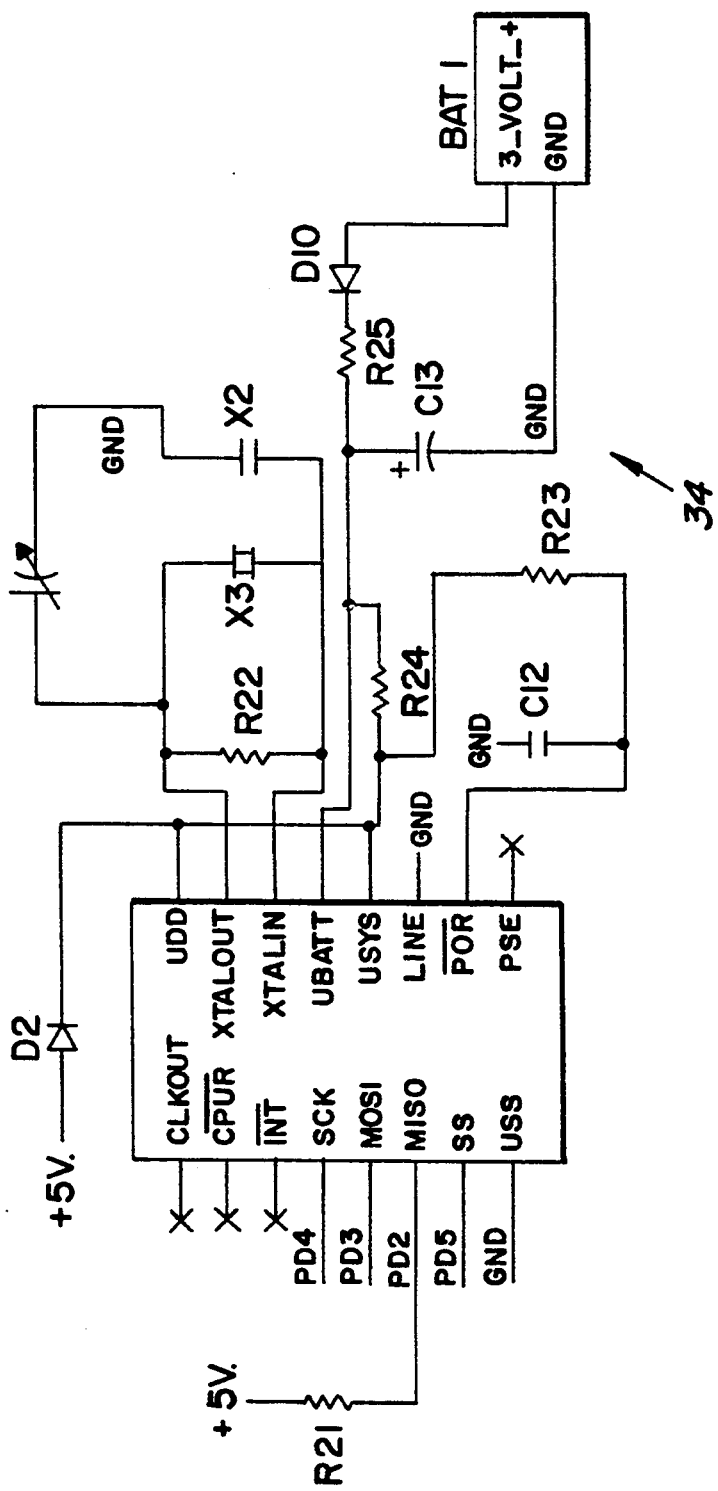
FIGS. 3a–e comprise a schematic diagram of one embodiment of the electronic controls and processing units of this invention.
Figure 3B:
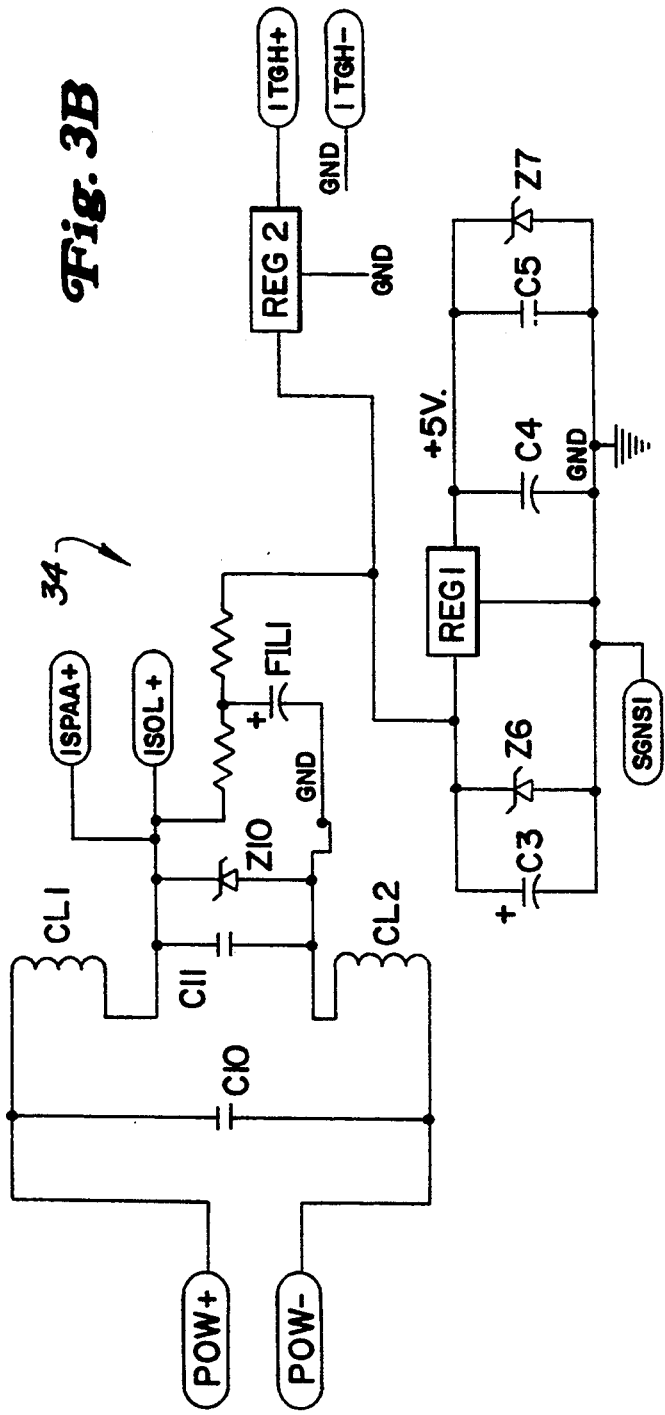
Figure 3C:
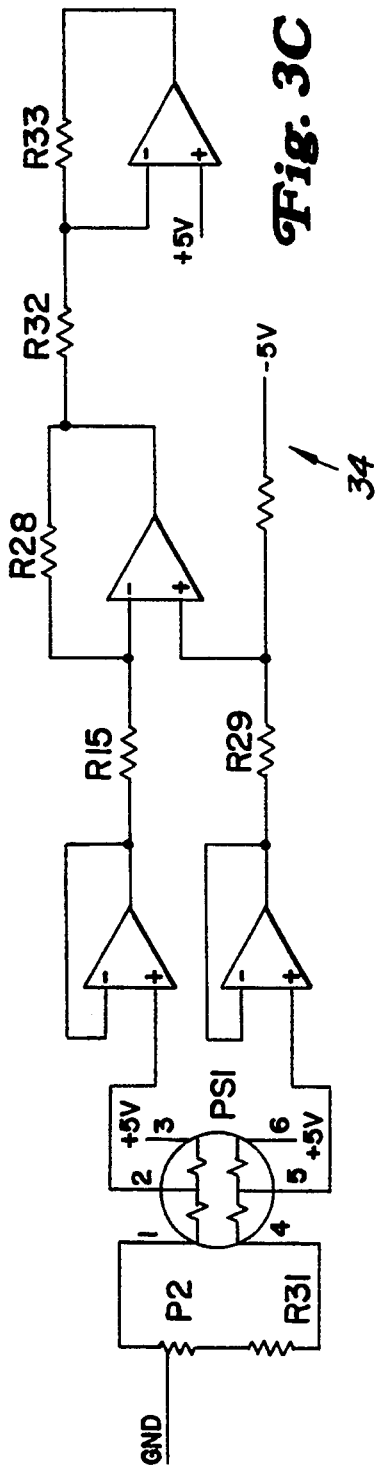
Figure 3D:
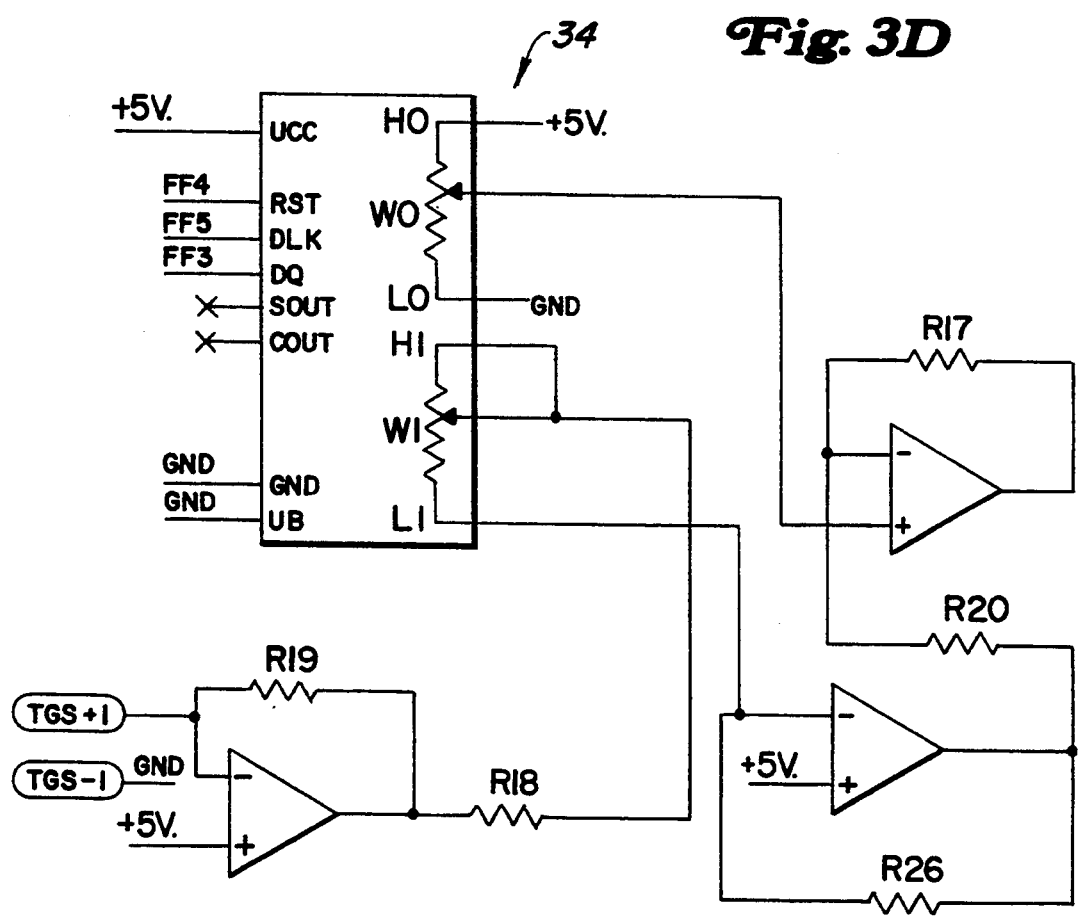
Figure 3E:
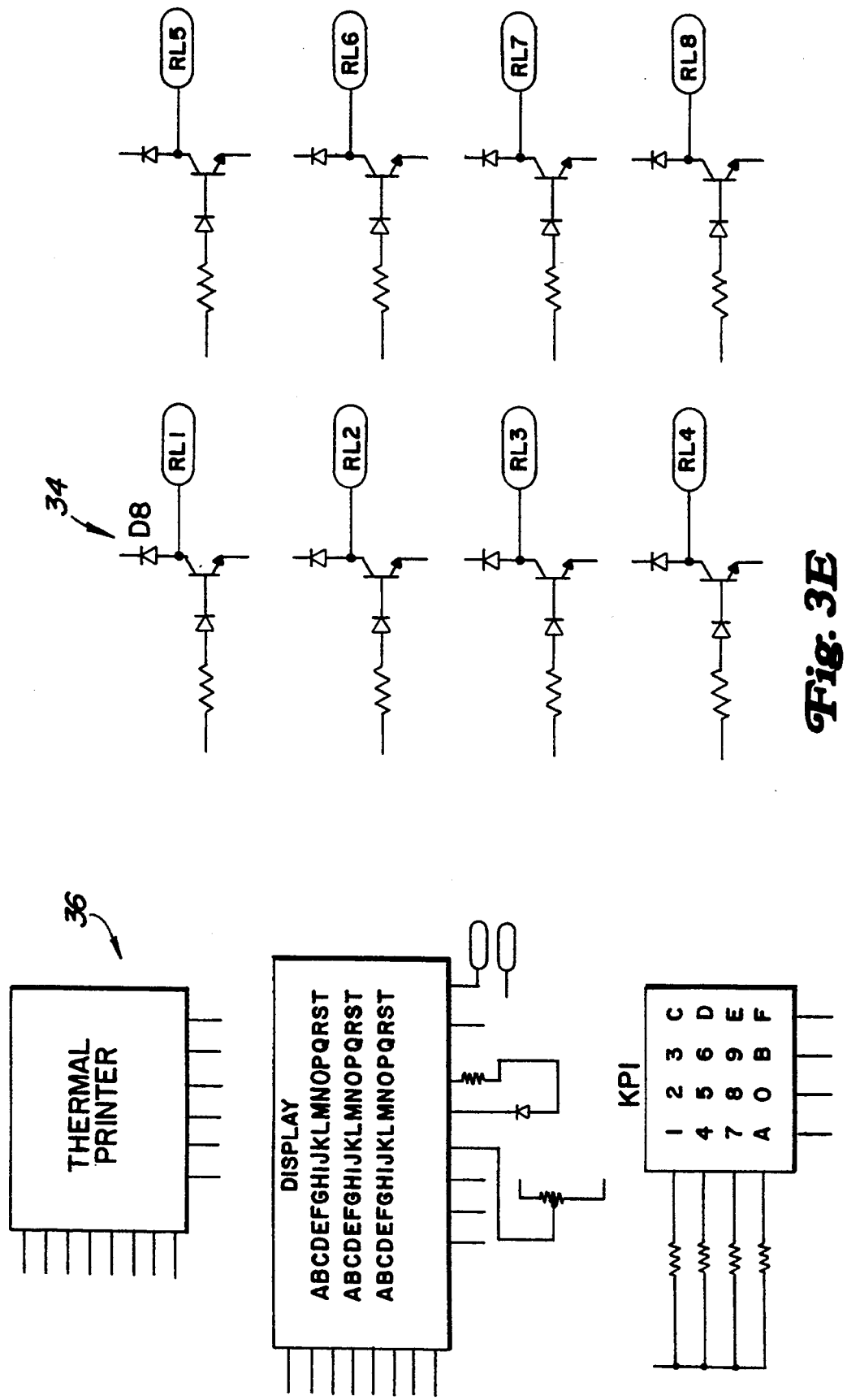

The operation of this system will now be described using FIGS. 1 and 2 basically with the requisite block diagram electronics (34) as shown in FIGS. 3a–e, schematically connected to the appropriate units in FIGS. 1 and 2. The unit has been turned on, after the self testing, it is ready to operate the test for the ethanol content of the breath of a person.

Once the operational sequence has been activated a step is called for by the program and performed, this step is known as the purge. This is to clear out any and all residue of gases remaining in the system and to insure a stable pathway in the pneumatics for the subsequent measurement of the suspect air or the breath of the person being tested. In this mode the fresh air inlet (14), and the solenoid (15), are in the closed position and fresh air passes through the blow tube (10), the blow exhaust (13), the sample exhaust (21), into the solenoid (24), out the vacuum pump (25), and the exhaust (26). This cleans all of the pneumatic pathways and isolates the chromatograph tube (22), and the sensor (23), which are not subject to being purged at this time. Then there is an additional internal cleansing system, i.e. a heat cleaning of the sensor only. This is programed in the processor (34), and is accomplished by increasing the voltage applied to the sensor (23), by some percentage to insure that the sensor is prepared and ready for the subsequent testing.

In the first operational step or mode called for next by the processor (34), the fresh air inlet (14), and the solenoid (15), are in the open position. The fresh air passes from the fresh air inlet (14) through the solenoid (16), through the sample tube (19), then through chromatograph tube (22), the sensor (23), the solenoid (24), vacuum pump (25) and out the exhaust (26). Passing the air through the chromatograph tube (22), and sensor (23), measures a reference value for the content of the ambient air. This is the first reference value and is utilized to establish a base for stabilizing the sensor and helps to insure accurate readings.

When the processor (34), determines that the first reference value has been established by evaluation in evaluation circuit in evaluation block, the value is stored in block for subsequent use.

At this point the process can instruct the person to be tested to blow into the blow tube (10) until the pressure sensor (11) determines that a sufficient amount of air has been put into the sample loop or tube (19). Prior to such volume being determined the blowing air is exhausted through blow exhaust (13) until the electronics in processor (34), including the pressure sensor, indicate that a sufficient volume has been blown so that the next volume blown by the person will contain the best breath sample for measurement of ethanol content. When such volume and pressure are reached, solenoid (15), and solenoid (24), will close momentarily, allowing the sample loop or tube to be filled with suspect air and any excess air blown by the person, will then again be exhausted by the blow exhaust (13). All of these functions are controlled automatically by the electronics of this system including processor (34).

Then the pre-determined sample of suspect air is passed through the chromatograph tube (22), and the sensor (23), and out through exhaust (26). The sample is sensed only during the window of time that ethanol is passed through chromatograph tube (22).

The reference value of the ethanol contained, i.e. the second reference value in this sample of suspect air is measured by the ethanol sensor and the value delivered to the electronics block for storage to be held and compared later.

The processor then initiates the next operational mode. The ambient or fresh air is introduced at inlet (14), and the solenoid (15) permits the air to flow through sample tube (19), solenoid (16), being open to the passage of the ambient air and closed to the introduction of the reference gas. The ambient air then enters into the sample loop (19). This sample loop (19) is of a pre-determined volume and is filled to capacity to always have a fixed sample of either ambient air or the suspect air possibly containing a pre-selected gas. The pre-determined amount of fresh or ambient air sample is then passed directly through the chromatograph tube (22), and past the sensor (23), and out exhaust (26). In passing the sensor (23), an output value is established for the content of that predetermined amount of ambient air. This is the third reference value and is also utilized to establish the base value to stabilize the sensor and help to insure accurate readings.

The processor now initiates next operational step, this step uses the reference gas from the reference gas source (18). This gas must pass through a pressure regulator (17), in order to insure that the operational limits of the chromatograph tubes and sensors are not exceeded. The reference gas is released to fill the pre-determined volume of the sample loop. The solenoid (16), and solenoid (20), operate to fill the sample loop. This predetermined volume of reference gas, once the sample loop is filled, is opened and the reference gas passes through the chromatograph tube (22), the ethanol sensor (23), and once again out through the exhaust (26) to establish the fourth reference value. This reference value is also stored in evaluation block, for subsequent use.

The processor (34), now initiates an integration function or it may be accomplished before storage of the time related values obtained from sensor (23). The integrated values are then fed to processor (34) for comparison.

Once the four reference values have been determined, the first reference value (i.e. the first ambient air value) is compared with the third reference value (i.e. The second passage of ambient air) past the sensor (23). The second reference value (the suspect air sample, possibly including ethanol) is compared to the fourth reference value (i.e. The pure reference gas, in this case ethanol). These two compared values then are mathematically integrated to determine the level of the preselected gas in the suspect's air sample by utilizing all of the reference values generated. The vagaries of the sensor are thus diminished because a plurality of time-related integrated values are compared to the variable content of percentage of the predetermined gas to be measured in the sample breath.

The processor (34) can now calculate accurately breath alcohol content of the suspect air using percent difference between suspect integrated value and ambient air and reference gas integrated value and ambient air. This blood alcohol content can now be displayed on any desired device or print out device (36). The signal could also be transmitted to remote display or read out by telephone, radio, satellite, etc.

The processor has an internal check on the validity, i.e. low voltage, low pressure reference gas, etc. and if reading is invalid will so indicate and will not display a value. A second check should be run after error is corrected. These errors are generally self-corrected, so that the machine remains operative over a long period of time.

This method permits the use of a single inexpensive sensor with wide changes of output due to volts, temperature, humidity, etc., to determine the value of the breath of the ethanol or any other desired gas in the presence of a mixture of gases, as long as the mixture contains elements of normal ambient air. This method of determining the ethanol content of a suspect air or, indeed determining the gas content of any mixture of gases containing a pre-determined gas will render a very accurate measure of the gas content.

Obviously numerous modifications and variations of the present invention are possible in light of the above teachings. It is to be specifically understood that it will be possible to vary the values of units to sense pre-determined levels of almost any gas in almost any environment and to signal the level sensed. It is, there fore, to be understood that within the scope of the appended claims that the invention may be practiced otherwise than is specifically described herein.

We claim:

1. A gaseous detection system for detecting the presence and determining the level of a preselected gas in a mixture of gases comprising:

isolation means having an input for receiving a mixture of gases, including a preselected gas, including an output means for providing a sequential flow of substantially segregated gases contained in said mixture of gases, such that the preselected gas contained within said mixture of gases is provided in substantially isolated form at said output during a preselected window of time following the introduction of said mixture of gases to said input of said isolation means;

sensor means responsive to the preselected gas and which provides an electric signal indicative of the presence and an amount of said preselected gas;

a source of ambient air;

a source of reference gas;

a source of sample air;

a sample loop of fixed volume;

a plurality of exhaust vents;

pneumatic pathways interconnecting said sources of air, said sources of reference gas, said loop, said sensor means, and said isolation means;

a plurality of valve means for selectively connecting in a predetermined order said sources of air, said sources of reference gas, said loop, said sensor means, and said isolation means by the various pneumatic pathways;

control means to selectively and sequentially operate in said predetermined order, said valve means to generate a plurality of signals;

said control means first, serially connects said ambient air by said valves to said sample loop, said isolation means, said sensor means, and a first exhaust outlet to generate a first signal in said sensor means;

said control means secondly, serially connects said source of sample air by said valves to said sample loop, said isolation means, said sensor means, and said first exhaust outlet to generate a second signal in said sensor means;

said control means thirdly, serially connects said source of ambient air for a second time by said valves, to said sample loop, said isolation means, said sensor means, said first exhaust outlet to generate a third signal in said sensor means;

said control means fourthly, serially connects said source of reference gas by said valves, to said sample loops, said isolation means, said sensor means to said first exhaust outlet to generate a fourth signal in said sensor means; and means for processing said plurality of signals to generate a signal indicative of the amount of said preselected gas in said source of sample air.

2. A gaseous detection system as in claim 1, wherein said processing means includes means for integrating signals, means for storing signals, means for evaluating and comparing signals, and means for generating output signals indicative of the result of said integration evaluation and comparing of said signals.

3. A gaseous detection system as in claim 1, wherein said means for integrating signal is constructed to integrate each of said signals generated in said sensor means.

4. A gaseous detection system as in claim 3, wherein said means for evaluating and comparing signal is constructed to compare the first integrated signal to the third integrated signal and generates a fifth signal.

5. A gaseous detection system as in claim 4, wherein said means for evaluating and comparing signals is constructed to compare the second integrated signal to the fourth integrated signal and generates a sixth signal.

6. A gaseous detection system as in claim 5, wherein means for integrating signals is constructed to integrate said fifth and sixth signals to determine the amount of the preselected gas in said sample air and generate a signal indicative of the amount of said preselected gas.

7. A gaseous detection system as in claim 1, wherein said isolation means is a chromatograph tube.

8. A gaseous detection system as in claim 1, wherein said control means includes timing means and switching means connected to said valves and said processor.

* * * * *